United States Patent [19]

Davis et al.

[11] Patent Number: 5,683,248
[45] Date of Patent: Nov. 4, 1997

[54] AUTOCLAVING CAP FOR DENTAL HANDPIECES

[76] Inventors: Warren Davis, 942 E. El Dorado St., Las Vegas, Nev. 89119; Fred Renwald, 11447 Ruffner Ave., Granada Hills, Calif. 91344; Dale Niemiec, 5520 Red Bluff, Las Vegas, Nev. 89130

[21] Appl. No.: 555,833

[22] Filed: Nov. 13, 1995

[51] Int. Cl.$^6$ .............................. A61C 1/05; A61C 1/10; A61C 3/00

[52] U.S. Cl. .......................... 433/115; 433/114; 433/116; 433/132

[58] Field of Search ................... 433/104, 114, 433/115, 116, 25, 132

[56] References Cited

U.S. PATENT DOCUMENTS

| | | | |
|---|---|---|---|
| 684,951 | 10/1901 | Rothkranz | 433/116 |
| 866,518 | 9/1907 | Repsold | 433/116 |
| 1,356,352 | 10/1920 | Ganzalez | 433/116 |
| 1,821,451 | 9/1931 | Terry | 433/116 |
| 4,264,303 | 4/1981 | Rosander | 433/25 |
| 5,165,503 | 11/1992 | Hoffman | 433/114 |

*Primary Examiner*—Nicholas D. Lucchesi
*Attorney, Agent, or Firm*—Frederick Gotha

[57] ABSTRACT

An autoclaving collar having a distal end and a proximate end is presented for fastening to the proximate end of a conventional dental handpiece to protect the impeller of the handpiece from the corrosive environment of autoclaving or sterilization. The collar has an opening at its distal end and an axially extending cavity that communicates with the opening and an annular shoulder which is concentric with the longitudinal axis of the collar for captively holding an O-ring member which seals the proximate threaded end of the conventional dental handpiece when the collar having internal mating thread is sufficiently threaded onto the proximate end of the dental handpiece.

19 Claims, 2 Drawing Sheets

AUTOCLAVING CAP FOR DENTAL HANDPIECES

FIELD OF THE INVENTION

This invention relates to an internally threaded cap for sealing the proximate end of a conventional dental handpiece to protect the impeller against corrosion during autoclaving or sterilization of the handpiece.

BACKGROUND OF THE INVENTION

Conventional dental handpieces house pneumatic impellars or turbines which may operate at either high or slow speed for imparting rotation to the rotary cutting instrument or bur. Cutting instruments are commonly used in dentistry and consist of a small shaft and a head designed in various shapes which may be used at different rotational speeds to remove decay or shape cavities. Conventional handpieces have intake and exhaust air nozzles located at the proximate end of the handpiece which are connected to a pneumatic source to drive the impeller at a desired rotational speed. During sterilization or autoclaving of the handpiece, the pneumatic source connecter is removed from the intake and exhaust air nozzles thereby opening the fluid communication path to the impeller and exposing the impeller to corrosion. Such corrosion results in rusting and pitting of the impeller or turbine wheel and thus limits the life of the turbine. Thus, it is desirable to seal the intake and exhaust air nozzles and the coolant air and coolant water nozzles such that during the sterilization or autoclaving process, the turbine or impeller is isolated from disinfectant vapors.

SUMMARY OF THE INVENTION

The present invention is directed to a protective autoclaving cap which is internally threaded for mating with the external threads of a conventional dental handpiece at its proximate end. A first counterbore is contained within the autoclaving cap adjacent the thread run-out of the internal threads for holding a rubber or Teflon O-ring. A second counterbore is contained within the autoclaving cap adjacent the first counterbore where the second counterbore has a diameter which is less than the diameter of the first counterbore; and where the diameter and depth of the second counterbore are sufficiently dimensioned to enclose the air intake and exhaust nozzles and air and water coolant nozzles extending proximately from the proximate end of the handpiece. The difference in diameters between the first counterbore and second counterbore provides a circumferential shoulder against which the O-ring bears and permits compression of the O-ring when the autoclaving cap is threaded onto the proximate end of the conventional dental handpiece thereby providing a seal against the flow of disinfectant into the second counterbore thereby sealing the intake and exhaust air nozzles and coolant air and water nozzles extending from the proximate tip of the conventional dental handpiece.

In the preferred embodiment the autoclaving cap can be made of either a metal or plastic material and a third counterbore is utilized at the distal end of the cap where the third counterbore has a depth of at least 2 ½ times the pitch of the internal threads thereby assuring thread engagement with the mating threads of the threaded proximate end of the conventional dental handpiece sufficiently to assure compression of the O-ring. In another embodiment, the autoclaving cap may be made of a rubber material having internal threads and an O-ring which has a compressibility that is greater than the compressibility of the rubber autoclaving cap, i.e., the O-rings are made of an elastic material which is softer than the rubber autoclaving cap thereby resulting in compression of the O-ring to seal the proximate extension of the air intake and exhaust nozzles and water coolant and exhaust nozzles.

An autoclaving cap, therefore, for sealing the proximate extensions of the air intake and exhausts nozzles from a conventional dental handpiece is provided where the autoclaving cap fastens to the proximate external threads of the conventional handpiece and seals the conventional handpiece from the corrosive fluids which may be introduced upon cold sterilization or autoclaving of the conventional handpiece.

BRIEF DESCRIPTION OF THE DRAWINGS

These and other features and advantages will become appreciated as the same become better understood with reference to the following specification, claims and drawings wherein:

DETAILED DESCRIPTION

Figure 1:
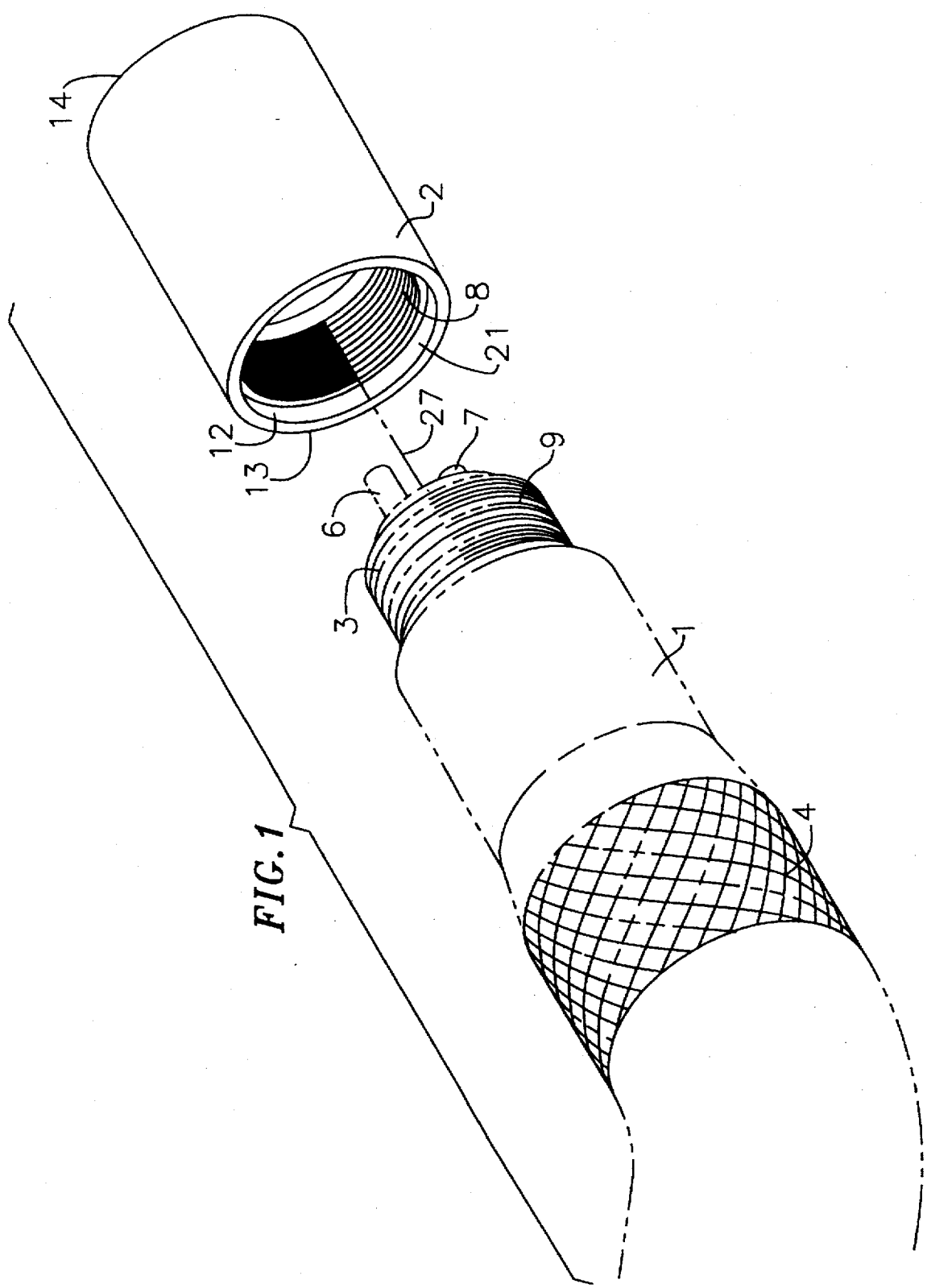
FIG. 1 is a perspective view illustrating the proximate end of a conventional dental handpiece and the autoclaving cap of this invention.

Referring now to FIG. 1, the proximate portion of a conventional dental handpiece 1 is shown in phantom lines and autoclaving cap 2 is illustrated in a removed position from the proximate end 3 of the dental handpiece. Conventional dental handpieces of the type illustrated in FIG. 1 are adapted to be gripped by the dentist by a knurled portion 4 and have an air intake nozzle 6 and an air exhaust nozzle 7 extending proximately from the proximate end 3 of the handpiece. Although not shown in the drawings, air intake nozzle 6 is in fluid communication with an impeller; the air intake nozzle delivers air for rotating the impeller which in turn is associated with a chuck to hold a bit or bur that is rotated at very high speeds due to the turbine type action as the intake air flows through the impeller. An example of a conventional dental handpiece is described in U.S. Pat. No. 4,884,968. Again, although not shown in the drawings, an air supply connector which connects to air intake nozzle 6 and which also contains a conduit for exhaust air from air exhaust nozzle 7 is removably mountable to the proximate end 3 of the handpiece. In the prior art, prior to sterilization or autoclaving the air supply connector is disconnected from the proximate end 3 of the dental handpiece thereby creating an open communication channel through both the air intake nozzle and air exhaust nozzle to the impeller. This open channel permits fluid access to the impeller and limits the life of the impeller by corrosive fluid contact with the impeller over successive sterilization or autoclaving exposures.

Referring again to FIG. 1, it can be seen that autoclaving cap 2 has internally mating threads 8 which mate with external threads 9 located at the proximate end of the conventional dental handpiece. Autoclaving cap 2 is more clearly shown in cross-section in FIG. 2.

Figure 2:
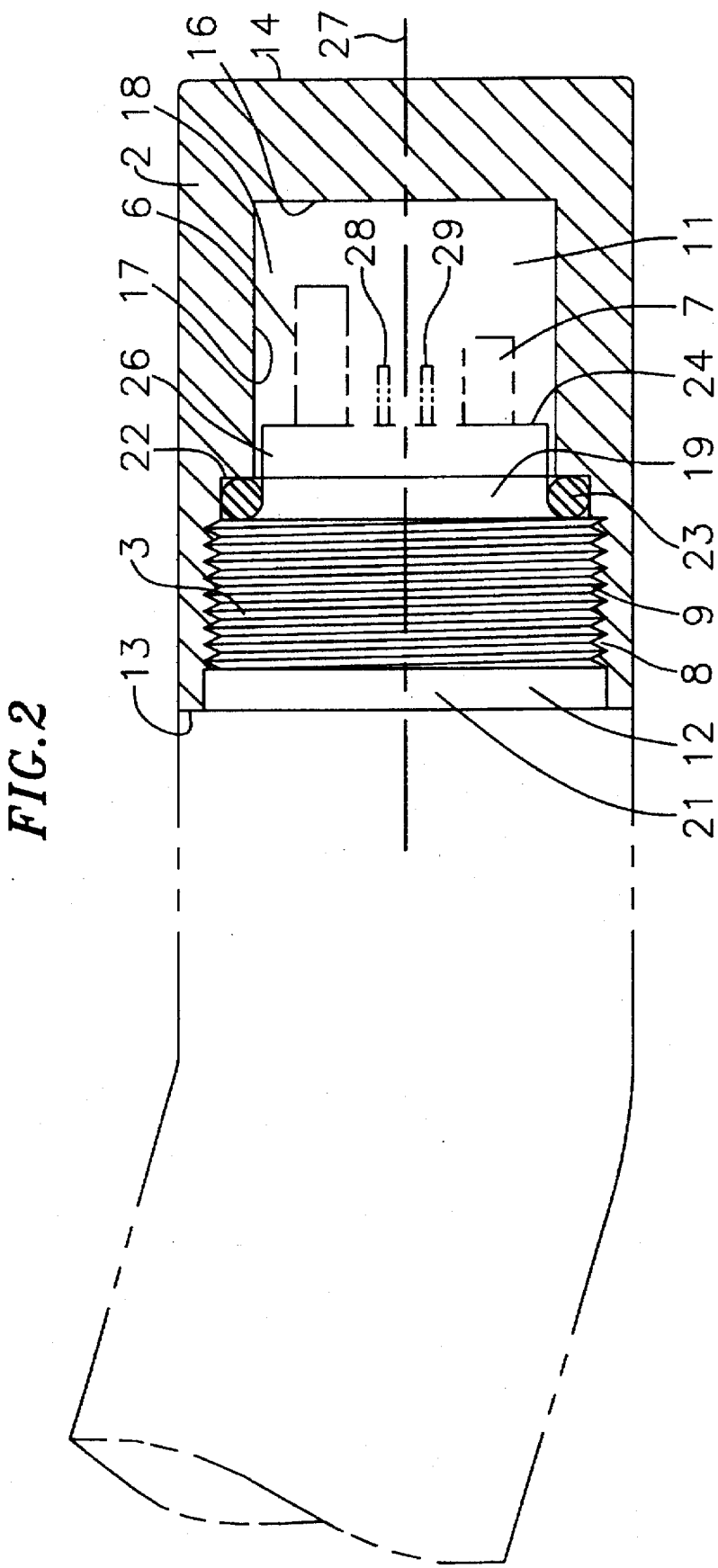
FIG. 2 is a cross-sectional view of the autoclaving cap fastened to the proximate end of the conventional dental handpiece where the air intake and exhaust nozzles and coolant air and water nozzles are shown in phantom.

FIG. 2 depicts autoclaving cap 2 after it is threaded on to the distal end 3 of the conventional dental handpiece. As can be seen in FIG. 2, autoclaving cap 2 is a collar with a cavity 11 which has an opening 12 located in the distal end 13 of autoclaving cap 2. At the proximate end 14 of the autoclaving cap, it can be seen that cavity 11 is bounded radially by neck portion 16 and bounded internally by the axially extending boundary wall 17.

In the preferred embodiment, cavity 11 consists of a series of counterbores, namely, first counterbore 18, second counterbore 19 and third counterbore 21. Referring again to FIG. 2, it can be seen that at the intersection of the first and second counterbores, a circumferential shoulder 22 is defined and forms the seat for toroidal seal member 23. As can more clearly be seen in FIG. 2, at the proximate end 3 of the conventional handpiece a protruding section 24 extends proximately from the threads 9 and has a enclosing circumferential wall 26 against which toroidal seal 23 sealingly bears where the radial direction is relative to horizontal axis 27. Thus, when circumferential shoulder 22 compressibly bears against toroidal seal 23 as the autoclaving cap is tightened, the first counterbore cavity 18 seals air intake nozzle 6 and also air exhaust nozzle 7 which prevents fluid from entering through these nozzles during the sterilization or autoclaving process thereby sealing the impeller of the dental handpiece from the corrosive effects of the autoclaving or sterilization process.

Conventional dental handpieces contain water intake nozzles 28 and water exhaust nozzles 29 which also project proximately from protruding section 24 and these nozzles will also be sealed by tightening the autoclaving cap to and thus compressing toroidal seal member 23. Toroidal seal 23 in the preferred embodiment is an O-ring made of rubber; in another embodiment toroidal seal member 23 may be made of a "Teflon" a trademark of Dupont Company, material. In construction, autoclaving cap member 2 may be made of a rubber, ceramic or metal material and in the preferred embodiment has internal threads such as shown in FIGS. 1 and 2. The proximate end of a conventional dental handpiece in some instances may be grooved rather than threaded thus providing an alternative fastening means for the air supply source which may contain locking grooves to permit mating of the air supply source with the proximate end of the dental handpiece.

As can be seen in the Figures, second counterbore 19 is integrally threaded and communicates with the third counterbore 21. Third counterbore 21 of the invention prevents cross-threading to occur and assures complete thread mating between the external threads of the conventional dental handpiece and the internal threads of the autoclaving autoclaving cap.

Thus, an autoclaving cap has been described in combination with a conventional dental handpiece where the autoclaving cap is internally threaded and contains an O-ring that circumferentially seals circumferential wall 26 of the proximate end 3 of the handpiece upon axial compression of the toroidal member. This in turn seals the air intake and exhaust nozzles of the dental handpiece and prevents the disinfectant elements of a sterilization or autoclaving environment from corroding the impeller thereby extending the life of the impeller and consequently the handpiece itself.

While I have shown and described an autoclaving cap to be fastened to the proximate end of a conventional dental handpiece to reduce the corrosive effects of sterilization or autoclaving environment on the handpiece impeller, it is to be understood that the invention subject to many modifications without departing from the scope and spirit of the claims as recited herein. This invention is not to be limited by the embodiment shown in the drawings and described in the description which is given by way of example and not of limitation.

What is claimed is:

1. In combination with a dental handpiece of the type having a fluid intake nozzle and a fluid exhaust nozzle extending from the proximate end of said dental handpiece, said dental handpiece further having an impeller in fluid communication with said fluid intake nozzle rotationally responsive to fluid flow through said fluid intake nozzle for rotating a dental bur, and where said proximate end of said dental handpiece is so configured and constructed to permit an air supply source to be removably fastened to said proximate end, an autoclaving cap comprising a collar having a peripheral surface, a longitudinal axis, and a distal end and a proximate end, said collar further having an axially extending enclosed cavity bounded by said peripheral surface and having an opening at said distal end communicating with said enclosed cavity, an annular shoulder concentric with said longitudinal axis integrally contained within said collar and located intermediate said distal and proximate ends of said collar, a toroidal seal member made of an elastic compressible material captively held within said collar in bearing relationship with said shoulder for compressive engagement with said shoulder and so dimensioned and proportioned to seal said fluid intake nozzle and said fluid exhaust nozzle from fluid flow at said proximate end of said dental handpiece upon axial insertion of said proximate end of said dental handpiece into said cavity and upon axial compression of said toroidal seal member against said shoulder, and fastening means associated with said collar for fastening said collar to said proximate end of said dental handpiece such that said collar may be axially advanced relative to said proximate end of said dental handpiece thereby compressing said toroidal seal member against said shoulder and sealing said fluid intake nozzle and said fluid exhaust nozzle from fluid flow at said proximate end of said dental handpiece.

2. The combination recited in claim 1 wherein said cavity consists of a first counterbore and a second counterbore where said first counterbore is distally spaced from said second counterbore and has a diameter greater than said second counterbore, said annular shoulder being defined by the juncture of said first and second counterbores.

3. The combination recited in claim 1 wherein said toroidal seal member is an O-Ring.

4. The combination recited in claim 1 wherein said toroidal seal member is made of Teflon.

5. The combination recited in claim 1 wherein said toroidal seal member is made of a rubber material.

6. The combination recited in claim 1 wherein said proximate end of said dental handpiece is threaded and said fastening means comprises internal threads contained in said distal end of said collar.

7. The combination recited in claim 6 wherein said toroidal seal member is an O-ring.

8. The combination recited in claim 6 wherein said toroidal seal member is made of Teflon.

9. The combination recited in claim 6 wherein said toroidal seal member is made of a rubber material.

10. In combination:
  a) A dental handpiece of the type having an air intake nozzle and an air exhaust nozzle extending from the proximate end of said dental handpiece, said dental handpiece further having an impeller for imparting rotation to a dental bur where said impeller is in fluid communication with said intake nozzle and responsive to air flow through said air intake nozzle, and where said proximate end of said dental handpiece is so configured and constructed to permit an air supply source to be removably fastened to said proximate end; and b) an autoclaving cap comprising a collar having a peripheral surface, a longitudinal axis, and a distal end and a proximate end, said collar further having an axially extending enclosed cavity bounded by said peripheral surface and having an opening at said distal end communicating with said enclosed cavity, an annulat shoulder concentric with said longitudinal axis integrally contained within said collar located intermediate said distal and proximate ends of said collar, a toroidal seal member made of an elastic compressible material captively held within said collar in bearing relationship with said shoulder for compressive engagement with said shoulder and so dimensioned and proportioned to seal said fluid intake nozzle and said fluid exhaust nozzle from fluid flow at said proximate end of said dental handpiece upon axial insertion of said proximate end of said dental handpiece into said cavity and upon axial compression of said toroidal seal member against said shoulder, and fastening means associated with said collar for fastening said collar to said proximate end of said dental handpiece such that said collar may be axially advanced relative to said proximate end of said dental handpiece thereby compressing said toroidal seal member against said shoulder and sealing said fluid intake nozzle and said fluid exhaust nozzle from fluid flow at said proximate end of said dental handpiece.

11. The combination recited in claim 10 wherein said cavity consists of a first counterbore and second counterbore where said first counterbore is distally spaced from said second counterbore and has a diameter greater than said second counterbore, said annular shoulder being defined by the juncture of said first and second counterbores.

12. The combination recited in claim 10 wherein said toroidal seal member is an O-Ring.

13. The combination recited in claim 10 wherein said toroidal seal member is made of a Teflon material.

14. The combination recited in claim 10 wherein said toroidal seal member is made of a rubber material.

15. The combination recited in claim 10 wherein said proximate end of said dental handpiece is threaded and said fastening means comprises internal threads contained in said distal end of said collar.

16. The combination recited in claim 15 wherein said toroidal seal member is an O-ring.

17. The combination recited in claim 15 wherein said toroidal seal member is made of Teflon.

18. The combination recited in claim 15 wherein said toroidal seal member is made of rubber.

19. An improved method for protecting the impeller of a conventional dental handpiece from corrosive autoclaving fluid where the dental handpiece is of the type having a threaded proximate end, an air intake nozzle and an air exhaust nozzle extending proximately from said proximate end of said dental handpiece and in fluid communication with said impeller, comprising the steps of fastening a collar having an open end and a closed end and an internal annular shoulder intermediate said open and closed ends and a seal member in bearing engagement with said internal shoulder where said seal member is so dimensioned and proportioned to seal said proximate end of said handpiece, inserting said proximate end of said dental handpiece into said collar, and compressing said seal member against said internal annular shoulder sufficiently to preclude the flow of said autoclaving fluid to said impeller.

\* \* \* \* \*